United States Patent
Bramati et al.

(10) Patent No.: US 6,992,046 B2
(45) Date of Patent: Jan. 31, 2006

(54) CONCENTRATED AQUEOUS PHYTOPATHOLOGICAL FORMULATION COMPRISING A HERBICIDE AND A BETAINE TYPE SURFACTANT

(75) Inventors: Valerio Bramati, Arese (IT); Joël Coret, Robbinsville, NJ (US); Scott Edwards, Mt. Eliza (AU); Paul Gioia, Hillside (AU)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/866,389

(22) Filed: Jun. 12, 2004

(65) Prior Publication Data

US 2004/0224846 A1    Nov. 11, 2004

Related U.S. Application Data

(63) Continuation of application No. 10/059,708, filed on Jan. 29, 2002, now abandoned.

(51) Int. Cl.
*A01N 25/30* (2006.01)
*A01N 57/02* (2006.01)
(52) U.S. Cl. ...................... 504/206; 504/365
(58) Field of Classification Search ............... 504/206, 504/365
See application file for complete search history.

(56) References Cited

U.S. PATENT DOCUMENTS

| 5,341,932 | A | 8/1994 | Chen | 206/524 |
| 5,863,863 | A | 1/1999 | Hasebe | 504/116 |
| 5,912,209 | A | 6/1999 | Kassebaum | 504/206 |
| 5,998,332 | A | 12/1999 | Sato | 504/127 |
| 6,500,784 | B1 | 12/2002 | Mille | 504/206 |
| 6,653,257 | B2 | 11/2003 | Mille | 504/206 |

FOREIGN PATENT DOCUMENTS

| EP | 0 483 095 | 4/1992 |
| EP | 0 508 022 | 10/1992 |
| WO | WO 97/01281 | 1/1997 |
| WO | WO 99/45780 | 9/1999 |
| WO | WO 00/38523 | 7/2000 |
| WO | WO 01/08482 | 2/2001 |
| WO | WO 01/17358 | 3/2001 |
| WO | WO 01/26463 | 4/2001 |

*Primary Examiner*—S. Mark Clardy

(57) ABSTRACT

The present invention concerns an aqueous phytopathological formulation comprising a hydrosoluble salt of at least one aminophosphate or aminophosphonate type herbicide; at least one principal surfactant selected from alkylbetaines and alkyl(amidoalkyl)betaines, and at least one additive selected from at least one of the following compounds:
(i) amines or etheramines comprising at least one hydrocarbon radical containing 2 to 24 carbon atoms, optionally polyalkoxylated;
(ii) acid or non acid phosphate mon- or di-esters, optionally polyalkoxylated;
(iii) alkali metal, alkaline-earth metal, ammonium, alkylammonium, alkanolammonium, iron, zinc or manganese salts of a mineral acid.

16 Claims, No Drawings

CONCENTRATED AQUEOUS PHYTOPATHOLOGICAL FORMULATION COMPRISING A HERBICIDE AND A BETAINE TYPE SURFACTANT

This application is a continuation of U.S. application Ser. No. 10/059,708, filed on Jan. 29, 2002 now abandoned.

The present invention relates to aqueous phytopathological formulations comprising at least one aminophosphate or aminophosphonate type herbicide and at least one betaine type principal surfactant associated with one or more particular additives.

Among the various normal presentations of phytopathological formulations that can be cited are concentrated aqueous formulations which are diluted by the user prior to applying them to the plants to be treated.

In addition to the active ingredient or ingredients, such aqueous formulations comprise additives known as biological activators the role of which is to increase the efficacy of the herbicide, for example by encouraging wetting of the plant by that active ingredient or by encouraging penetration into the plant.

Particularly regarding aqueous commercial formulations comprising active ingredients of the amino acid type cited above, one of the most frequently used biological activators is an ethoxylated amine.

The presence of these amines considerably strengthens the biological activity of the herbicide, most probably by activating diffusion of the herbicide through the cuticular barrier of the plant.

The major disadvantage with ethoxylated amine compounds is their chemical toxicity. They are irritants and are only slightly biodegradable. Further, they are highly ecotoxic, more particularly towards aquatic plant organisms (algae) or aquatic animals (insects, batrachia) even at low concentrations.

The ever more serious view taken of these different problems has led to a search for phytopathological compounds, preferably hydrosoluble phytopathological compounds, with a biological activity that is comparable to current formulations and with substantially reduced toxicity and ecotoxicity.

Thus, the present invention aims to provide novel aqueous phytopathological formulations comprising at least one active ingredient, more particular a herbicide of the aminophosphate or aminophosphonate type, with a proportion of ethoxylated amine with respect to the herbicide that is lower than in the normal formulations, or even free of such amines, while retaining an activity that is at least equal to said formulations.

These and other aims are accomplished by the present invention which thus concerns aqueous phytopathological formulations comprising a hydrosoluble salt of at least one aminophosphate or aminophosphonate type herbicide; at least one principal surfactant selected from alkylbetaines and alkyl(amidoalkyl)betaines, and at least one additive selected from at least one of the following compounds:
  (i) amines or etheramines comprising at least one hydrocarbon radical containing 2 to 24 carbon atoms, optionally polyalkoxylated;
  (ii) acid or non acid phosphate mono- or di-esters, optionally polyalkoxylated;
  (iii) alkali metal, alkaline-earth metal, ammonium, alkylammonium, alkanolammonium, iron, zinc or manganese salts of a mineral acid.

The particular choice of principal surfactant combined with at least one of the additives listed above can produce phytopathological formulations with a reduced ethoxylated amine content, or even formulations that are free of this type of compound while retaining a level of efficacy that is at least as good as that achieved with commercially available formulations.

The consequences of this reduction in the amount of ethoxylated amine are to be found in the significant reduction in the toxicity of the final formulation itself. These characteristics are still further improved when the formulation is free of that amine.

Further, the formulation of the invention is stable on storage and does not cause problems during use. No gel appears, nor does the viscosity increase greatly during dilution prior to application.

Other advantages and characteristics of the present invention will become apparent from the following description and examples.

As indicated above, the formulation of the invention comprises, as an active ingredient, a hydrosoluble salt of at least one herbicide of the aminophosphate or aminophosphonate type.

Preferably, the formulations of the invention comprise at least one hydrosoluble salt of N-phosphonomethyl glycine.

The term "glyphosate" will be used below to define hydrosoluble salts of N-phosphonomethyl glycine.

Suitable salts that can more particularly be cited are the salts of alkali metals such as sodium or potassium; ammonium salts of the $N(R)_4^+$ type in which radicals R, which may be identical or different, represent a hydrogen atom or a linear or non linear, saturated or unsaturated $C_1$–$C_6$ hydrocarbon radical that may be substituted by a hydroxyl group; or sulphonium salts; said salts being present alone or in a combination.

Ammonium salts that can in particular be cited include secondary or primary amines such as isopropylamine, dimethylamine, diamines such as ethylenediamine, or alkanolamines such as monoethanolamine. Trimethylsulphonium is a perfectly suitable sulphonium salt.

Preferred glyphosate derivatives for herbicidal application that can be cited are isopropylamine, the monoethanolamine salt and the trimethylsulphonium salt.

Advantageously, the herbicide content of the aqueous formulations of the invention is in the range 80 to 510 g/l expressed in acid herbicide equivalents.

In accordance with one essential feature of the invention, the aqueous formulations comprises at least one principal surfactant selected from alkylbetaines and alkyl(amidoalkyl)betaines.

Preferably, the principal surfactant corresponds to one or more of the following formulae:

(I)

(II)

(III)

(IV)

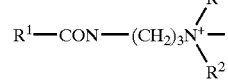

in which formulae:

R$^1$ represents a linear or branched alkyl group containing 3 to 30 carbon atoms, preferably 3 to 20 carbon atoms, such as propyl, dodecyl, hexadecyl or an alkamide group, such as dodecanamide;

R$^2$, which may or may not be identical, represent an alkyl radical, preferably a methyl radical;

R$^3$ represents a hydrogen atom or a —CH$_2$COOM radical or an alkyl radical;

M represents an alkali metal, preferably sodium.

Said compounds, which can be used in the invention as principal surfactants, are commercially available products and are sold by Rhodia Chimie under the trade names Mirataine® and Wettem®. Advantageously, said commercially available products can be used as they are, without undergoing an initial treatment to reduce the amount of salt, for example (sodium chloride in particular).

The amount of principal surfactant in the phytopathological formulation of the invention is advantageously in the range 20 to 180 g/l.

In addition to the principal surfactant, the phytopathological formulations of the invention comprise at least one additive selected from at least one of the following compounds:

(i) amines or etheramines comprising at least one hydrocarbon radical containing 2 to 24 carbon atoms, optionally polyalkoxylated;

(ii) acid or non acid mono- and di-ester phosphates, optionally polyalkoxylated;

(iii) alkali metal, alkaline-earth metal, ammonium, alkylammonium, alkanolammonium, iron, zinc or manganese salts of a mineral acid.

In accordance with a first possibility, compounds (i) are more particularly selected from amines comprising at least one linear or branched, saturated or unsaturated radical containing 2 to 24 carbon atoms, preferably 8 to 18 carbon atoms, optionally comprising 2 to 30 oxyalkylene motifs, preferably oxyethylene, or a mixture of a plurality thereof.

In accordance with a second possibility, compounds (i) are selected from etheramines comprising at least one linear or branched, saturated or unsaturated radical containing 6 to 24 carbon atoms, preferably 8 to 20 carbon atoms, optionally comprising 2 to 30 oxyalkylene motifs, preferably oxyethylene, or a mixture of a plurality thereof. More particularly, the etheramines correspond to the following formula:

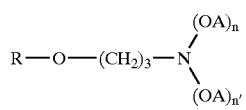

in which formula R represents a linear or branched, saturated or unsaturated hydrocarbon radical containing 6 to 24 carbon atoms, preferably 8 to 20 carbon atoms; OA, which may or may not be identical from one motif to another and from one branch to another, represent an oxyethylene motif, preferably oxypropylene; and n, n', which may or may not be identical, represent a mean number in the range 1 to 30.

Examples of such amines that can be cited are amines derived from copra and containing 5 oxyethylene (OE) motifs, oleic amines containing 5 OE, amines derived from tallow containing 10 OE, etheramines corresponding to the above formula, in which radical R is an alkyl radical containing 12 to 15 carbon atoms, the number of OE motifs being in the range 20 to 30.

It should be noted that highly advantageously, the amount of compounds (i) represents 0 to 120 g/l of the formulation. In a particular implementation of the invention, the amount of this type of compound is in the range 0 to 60 g/l. Preferably, the phytopathological formulations are free of them.

Turning now to compounds (ii), these are preferably selected from acid or non acid phosphate mono- or di-esters, optionally polyalkoxylated, with formula (II) below:

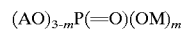

in which:

A, which may or may not be identical, represent a group R$^{'1}$—O(CH$_2$—CHR$^{'2}$—O) in which:

R$^{'1}$, which may or may not be identical, represent a linear or non linear, saturated or unsaturated C$_6$–C$_{20}$ hydrocarbon radical, preferably C$_8$–C$_{18}$;

R$^{'2}$, which may or may not be identical, represent a hydrogen atom or a methyl or ethyl radical, preferably a hydrogen atom;

n is a mean number of motifs in the range 0 to 10, preferably in the range 2 to 10;

M, which may or may not be identical, represent a hydrogen atom, an alkali or alkaline-earth metal, a N(R$^3$)$_4^+$ type radical in which radicals R$^3$, which may or may not be identical, represent a hydrogen atom or a linear or non linear, saturated or unsaturated C$_1$–C$_6$ hydrocarbon radical optionally substituted with a hydroxyl group;

m is a whole number in the range 1 to 2.

It should be noted that compound (ii) can be in the form of a monoester, a diester, or a mixture of these two esters.

Further, the amount of compound (ii), if present in the formulation of the invention, is in the range 0 to 120 g/l.

Compound (iii) is advantageously selected from alkali metal or alkaline-earth metal, ammonium, or linear or non linear, saturated or unsaturated C$_1$–C$_6$ alkylammonium or alkanolammonium sulphates, nitrates or phosphates; or from iron, zinc or manganese sulphates, used alone or as a mixture.

Finally, the amount of compound (iii) in the formulations, if present, is more particularly in the range 0 to 200 g/l.

In accordance with a preferred characteristic of the invention, the proportion by weight of principal surfactant/sum of additives (i) to (iii) is in the range 6/1 to 1/2.

Further, in one implementation of the invention, the total amount of principal surfactant and additive(s) represents 60 to 180 g/l of the formulation.

The formulations can also comprise additives that are conventional in the field such as anti-foaming agents, for example organopolysiloxanes; or thickening agents such as xanthan gum type polysaccharides, alginates, carboxylated or hydroxylated methylcelluloses, synthetic macromolecules of the polyacrylate, polymaleate, polyvinylpyrrolidone, polyethylene glycol or polyvinyl alcohol type, or of the inorganic type such as bentonites.

The formulation can also comprise auxiliary additives such as antioxidants, anti-UV agents, colorants, etc.

The amount of these additives listed above is normally less than 10% by weight, preferably 1% by weight or less, advantageously 0.1% by weight or less compared with the composition weight.

The compositions of the invention can be prepared by mixing their different constituents with moderate stirring.

This operation preferably takes place at a temperature in the range 15° C. to 60° C., preferably at a temperature close to ambient temperature (15–30° C.).

Usually, the principal surfactant is preferably only added once the other constituents have been mixed.

The phytopathological formulations of the invention are thus used to treat plants, normally after diluting with water.

Non-limiting examples of the invention will now be described.

EXAMPLE 1

A mixture with the following composition was prepared in water:

| | |
|---|---|
| *glycosphosate isopropylamine salt (46% acid) | 360 g/l |
| *Mirataine ® D40(*) | 80 g/l |
| *Geronol ® CF/AR (**) | 20 g/l |
| *oleic amine containing 5 OE motifs | 20 g/l |

(*)Mirataine ® D40 (sold by Rhodia Chimie): lauryldimethylbetaine.
(**)Geronol ® CF/AR (sold by Rhodia Geronazzo) is a mixture of mono- and di-ester phosphates with formula (I) from saturated $C_4$–$C_{10}$ aliphatic alcohols and comprising a mean of 3 to 8 motifs of ethylene oxide, and M is isopropyl ammonium.

A composition was obtained the efficacy of which was equivalent to a composition comprising the same amount of glyphosate (expressed as the acid equivalent) and with a concentration of 180 g/l of ethoxylated oleic amine (15 motifs).

The formulation was stable on storage at ambient temperature and at 54° C.

EXAMPLE 2

A mixture with the following composition was prepared in water:

| | |
|---|---|
| *glycophsate isopropylamine salt (46% acid) | 360 g/l |
| *Wettem ® MEI(*) | 100 g/l |
| *ammonium sulphate | 19 g/l |

(*)Wettem ® MEI (sold by Rhodia Chimie): lauryldimethylbetaine.

A composition was obtained the efficacy of which was equivalent to a composition comprising the same amount of glyphosate (expressed as the acid equivalent) and with a concentration of 180 g/l of ethoxylated oleic amine (15 motifs).

The formulation was stable on storage at ambient temperature and at 54° C.

What is claimed is:

1. An aqueous phytopathological formulation comprising:
   a hydrosoluble salt of at least one aminophosphate or aminophosphonate herbicide, wherein the herbicide content is comprised between 80 and 510 g/l, expressed in acid herbicide equivalents,
   between 20 and 180 g/l of at least one principal surfactant alkylbetaine, having formula (I):

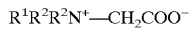
   $$R^1R^2R^2N^+\text{—}CH_2COO^-$$

wherein:
   $R^1$ represents a linear or branched alkyl group containing 3 to 30 carbon atoms or an alkamide group, and
   $R^2$, which is identical or different, represents an alkyl group, and
   one or more additive (i) being a polyalkoxylated amine having at least one hydrocarbon group containing from 2 to 24 carbon atoms.

2. A formulation according to claim 1, wherein the herbicide is a hydrosoluble salt of N-phosphonomethyl glycine.

3. A formulation according to claim 1, wherein:
   $R^1$ represents dodecyl, or hexadecyl, and
   $R^2$ represents methyl.

4. A formulation according to claim 1, wherein the additive (i), used alone or as a mixture, has at least one linear or branched, saturated or unsaturated group containing 8 to 18 carbon atoms, and presents 2 to 30 oxyalkylene motifs.

5. A formulation according to claim 4, wherein the oxyalkylene motifs are oxyethylene motifs.

6. A formulation according to claim 5, wherein additive (i), is an amine derived from tallow, containing 10 oxyethylene motifs.

7. A formulation according to claim 5, wherein
   $R^1$ represents dodecyl, or hexadecyl, and
   $R^2$ represents methyl.

8. A formulation according to claim 1, comprising up to 60 g/l of additive (i).

9. A formulation according to claim 7, comprising up to 60 g/l of additive (i).

10. A formulation according to claim 1, wherein the ratio by weight of principal surfactant/sum of additive (i), is comprised between 6/1 to 1/2.

11. A formulation according to claim 7, wherein the ratio by weight of principal surfactant/sum of additive (i), is comprised between 6/1 to 1/2.

12. A formulation according to claim 9, wherein the ratio by weight of principal surfactant/sum of additive (i), is comprised between 6/1 to 1/2.

13. A formulation according to claim 1, wherein the total amount of principal surfactant and additive (i), represents from 60 to 180 g/l of the formulation.

14. A formulation according to claim 12, wherein the total amount of principal surfactant and additive (i), represents from 60 to 180 g/l of the formulation.

15. A formulation according to claim 14, wherein the herbicide is a hydrosoluble salt of N-phosphonomethyl glycine.

16. A formulation according to claim 14, wherein the polyalkoxylated amine is present in a concentration up to 120 g/l.

* * * * *